United States Patent [19]

Hamprecht et al.

[11] Patent Number: 4,673,740
[45] Date of Patent: Jun. 16, 1987

[54] PREPARATION OF SUBSTITUTED 2-PHENYL-4H-3,1-BENZOXAZIN-4-ONES

[75] Inventors: Gerhard Hamprecht, Weinheim; Wolfgang Rohr, Wachenheim; Juergen Varwig, Heidelberg, all of Fed. Rep. of Germany

[73] Assignee: BASF Aktiengesellschaft, Ludwigshafen, Fed. Rep. of Germany

[21] Appl. No.: 842,995

[22] Filed: Mar. 24, 1986

[30] Foreign Application Priority Data

Apr. 19, 1985 [DE] Fed. Rep. of Germany ....... 3514183

[51] Int. Cl.$^4$ .......................................... C07D 265/36
[52] U.S. Cl. ...................................................... 544/92
[58] Field of Search .......................................... 544/92

[56] References Cited

U.S. PATENT DOCUMENTS

Re. 32,087 2/1986 Hamprecht et al. .......... 544/92 X
4,315,766 2/1982 Hamprecht et al. ................ 71/88
4,523,942 6/1985 Hamprecht et al. ................ 71/88

FOREIGN PATENT DOCUMENTS 1159060 12/1983 Canada .

OTHER PUBLICATIONS

J. Org. Chem. 9 (1944), 396.

X. Huang and Ch.-Ch. Chan in Synthesis, 1984 (10), 851–852.

Primary Examiner—Richard L. Raymond
Attorney, Agent, or Firm—Keil & Weinkauf

[57] ABSTRACT

2-Phenyl-4H-3,1-benzoxazin-4-ones of the general formula I

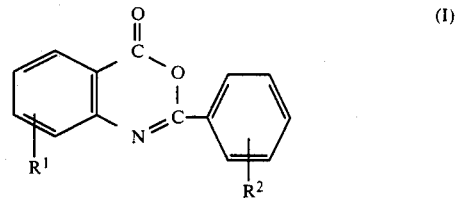

where $R^1$ and $R^2$ are each hydrogen or halogen, $R^1$ may furthermore be methyl or methoxy and $R^2$ may furthermore be haloalkyl, haloalkoxy, haloalkylmercapto or haloalkylsulfonyl, each of 1 to 3 carbon atoms, are prepared by reacting an appropriate anthranilic acid with an appropriate benzoyl halide in the presence of a base (acylation) and effecting ring closure by removal of water (cyclization), the process being carried out in a suspending agent which is immiscible with aqueous alkali metal hydroxide solution and in the presence of a phase-transfer catalyst.

4 Claims, No Drawings

PREPARATION OF SUBSTITUTED 2-PHENYL-4H-3,1-BENZOXAZIN-4-ONES

The present invention relates to a process for the preparation of substituted 2-phenyl-4H-3,1-benzoxazin-4-ones of the general formula I

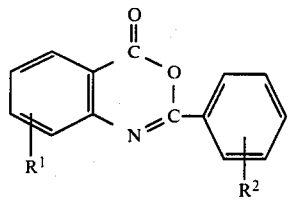

where $R^1$ and $R^2$ are each hydrogen or halogen, $R^1$ may furthermore be methyl or methoxy and $R^2$ may furthermore be haloalkyl, haloalkoxy, haloalkylmercapto or haloalkylsulfonyl, each of 1 to 3 carbon atoms, by reacting an appropriately substituted anthanilic acid and benzoyl halide in the presence of an inorganic acid acceptor or of a base.

If 6-chloroanthranilic acid and benzoyl chloride are used as starting materials, the course of the reaction can be represented by the following equation:

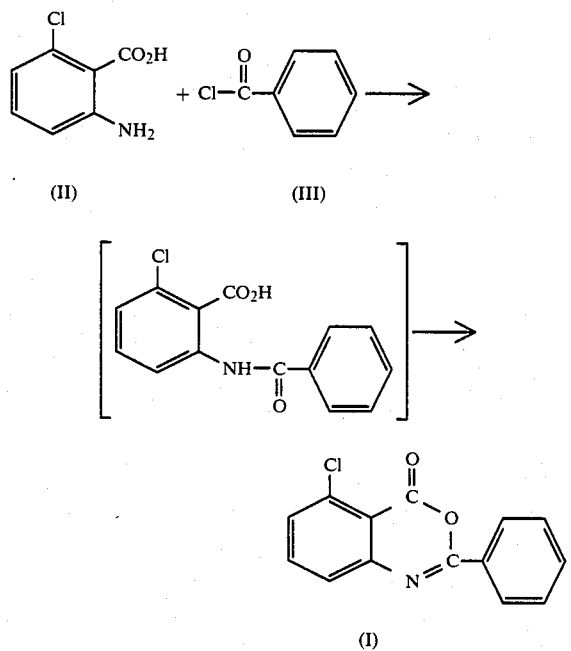

According to EP-A No. 17 931, it is also possible first to react an anthranilic acid with about the stoichiometric amount of a benzoyl halide and an organic base in an inert organic solvent to give the N-benzoylanthranilic acid, to purify the intermediate by treatment with hydrochloric acid and by extraction with an alkali and acidification, to dry this intermediate and then to subject it to a cyclization reaction with a cheap acyl halide or another dehydrating agent. Further washing with water is then carried out. The total yield is 60% (European Pat. No. 17,931, Example 2), 89% (European Pat. No. 32,242, Example 2) or 74% (German Laid-Open Application DOS No. 3,037,970, Example 2), depending on the pattern of substitution of the starting materials.

The space-time yield, as a measure of the cost-effectiveness of the process, is 0.105 kg per 1 per day just for the reaction time in both stages (European Pat. No. 17,931, Example 2). Owing to the various process steps required in the 1st stage, comprising extraction, reprecipitation, filtration under suction and drying and the distillation of the solvent itself, apart from the working up of the water-soluble base, a process which entails high losses, the space-time yield is reduced to about 0.05 kg per 1 per day. Another disadvantage from an industrial point of view is the occurrence of a dry dust-forming intermediate which is furthermore not very suitable for the further process stages.

In J. Org. Chem. 9 (1944), 396, a process for the benzoylation of anthranilic acid in dilute sodium hydroxide solution is described in detail. In this process, it is necessary to use highly dilute, e.g. 0.2 N, sodium hydroxide solution, since, at higher concentrations, the sodium salt of N-benzoylanthranilic acid crystallizes out and side reactions result in a lower overall yield. The reaction takes place slowly (for example over a period of 3 hours) and at a low reaction temperature and with thorough stirring, and requires not less than a two-fold excess of alkali. Because of the stated complications of the purification steps, which were also required and from which organic solvents must be excluded, this method designed for the laboratory appears to be unsuitable from an industrial point of view.

A process for the preparation of, inter alia, 3-oxo-3,4-dihydro-2H-1,4-benzoxazines in the presence of a phase-transfer catalyst is described by X. Huang and Ch.-Ch. Chan in Synthesis 1984 (10), 851–852. However, this process only appears to be similar to the invention described below, since it requires not less than the stoichiometric amount of a benzyltrimethylammonium salt.

It is an object of the present invention to provide a simple process for the preparation of 2-phenyl-4H-3,1-benzoxazin-4-ones of the formula I, which are satisfactory on an industrial scale.

We have found that this object is advantageously achieved by a process in which the anthranilic acid in an organic solvent which is immiscible with aqueous alkali metal hydroxide solution is initially taken, a stoichiometric amount of not less than 25% strength alkali metal hydroxide solution and a stoichiometric amount of a benzoyl halide are added simultaneously or in succession in the presence of a phase-transfer catalyst (acylation) and, after the water has been removed, the resulting N-benzoylanthranilic acid is subjected to a cyclization reaction in a conventional manner. Instead of the anthranilic acid, it is of course also possible to use one of its alkali metal salts; in this case, the addition of an alkali metal hydroxide solution can be dispensed with.

Compared with the prior art, the novel process gives 2-phenyl-4H-3,1-benzoxazin-4-ones in better yield and purity by a simpler and more economical route and is furthermore surprising in a number of respects.

As stated at the outset, the use of concentrated sodium hydroxide solution was expected to give a reduced yield as a result of the intermediate crystallizing out and side reactions occurring (e.g. hydrolysis of benzoyl halide), and it was necessary to avoid the use of an organic solvent.

As demonstrated by the above comparative experiment, substitution of the anthranilic acid, for example by halogen in the 6-position, results in a greatly reduced reaction rate, so that the method described in J. Org. Chem. gives the intermediate in a yield of only 71.5%.

Finally, as indicated above, it is well-known that benzoyl halides, which per se are poorly soluble in water, are rapidly hydrolyzed in the presence of solubilizing additives (organic solvents, e.g. ethers), especially when an aqueous alkali is present instead of water.

Contrary to expectations, however, the benzoyl halide reacts exclusively with the amino group of the anthranilic acid in the procedure according to the invention.

Also contrary to expectations, there is no need to carry out the reaction at a low temperature, with the associated expense of cooling energy, or to incur costs entailed by special stirring procedures, etc. Finally, the space-time yield of the novel process is several times higher than that of the conventional one.

Preferred starting materials II and III, and accordingly preferred end products I, are those of the formulae where $R^1$ and $R^2$ are each hydrogen or halogen. For economic reasons, the starting materials II and III should be used in stoichiometric amounts; an excess of one or other of the components, for example a ratio of from 0.9 to 1.1, in particular from 1 to 1.05, mole of starting material III per mole of starting material II, is however not disadvantageous industrially.

Examples of suitable 2-aminobenzoic acids (II) are anthranilic acid, 6-chloro-, 6-fluoro- and 6-bromoanthranilic acid, 6-methyl- and 6-methoxyanthranilic acid, 5-fluoro-, 5-chloro-, 5-bromo-, 5-methyl- and 5-methoxyanthranilic acid, 4-fluoro-, 4-chloro-, 4-bromo-, 4-methyl- and 4-methoxyanthranilic acid and 3-fluoro-, 3-chloro-, 3-bromo-, 3-methyl- and 3-methoxyanthranilic acid.

Examples of benzoyl halides (III) are benzoyl chloride and bromide, m- and p-fluorobenzoyl chloride, m- and p-chlorobenzoyl chloride, m- and p-trifluoromethoxybenzoyl fluoride, m- and p-chlorodifluoromethoybenzoyl fluoride, m- and p-difluoromethoxybenzoyl chloride, m- and p-trifluoromethylmercaptobenzoyl fluoride, m- and p-chlorodifluoromethylmercaptobenzoyl fluoride, m- and p-difluoromethylmercaptobenzoyl chloride, m- and p-1,1,2,2-tetrafluoroethoxybenzoyl chloride, m- and p-1,1,2-trifluoro-2-chloroethoxybenzoyl chloride, m- and p-1,1,2,2-tetrafluoroethylmercaptobenzoyl chloride, m- and p-chloromethylsulfonylbenzoyl chloride and m- and p-trifluoromethylsulfonylbenzoyl fluoride.

The acylation is carried out at from 10° to 50° C., preferably from 20° to 45° C., and any conventional process engineering measures, for example continuous or batchwise operation, stirred kettles, tube reactors, etc., may be used.

A predetermined amount of anthranilic acid or of one of its alkali metal salts in a water-immiscible organic suspending agent which is inert under the reaction conditions is initially taken in the presence of a phase-transfer catalyst. Particularly suitable organic suspending agents are chlorohydrocarbons, such as tetrachloroethylene, 1,1,2,2- and 1,1,1,2-tetrachloroethane, dichloropropane, methylene chloride, dichlorobutane, chloroform, chloronaphthalene, dichloronaphthalene, carbon tetrachloride, 1,1,1- and 1,1,2-trichloroethane, trichloroethylene, pentachloroethane, o-, m- and p-dichlorobenzene, 1,2-dichloroethane, 1,1-dichloroethane or 1,2dichloroethylene; chlorobenzene, fluorobenzene, bromobenzene, iodobenzene, o-, p- and m-dichlorobenzene, o-, p- and m-dibromobenzene, o-, m- and p-chlorotoluene and 1,2,4-trichlorobenzene; ethers, provided that they are not too water-soluble, e.g. ethyl propyl ether, methyl tert-butyl ether, n-butylethyl ether, di-n-butyl ether, diisobutyl ether, diisoamyl ether, diisopropyl ether, anisole, phenetole, cyclohexyl methyl ether or thioanisole; nitrohydrocarbons, such as nitromethane, nitroethane, nitrobenzene, o-, m- and p-chloronitrobenzene or o-nitrotoluene; hydrocarbons, e.g. heptane, pinane, nonane, o-, m- and p-cymene, gasoline fractions boiling within a range from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane, octane, toluene, xylene and mixtures of these; esters, e.g. ethyl acetate, ethyl acetoacetate or isobutyl acetate, and amides, e.g. 2-ethylhexanoic acid dimethylamide. Advantageously, the solvent is used in an amount of from 1,000 to 3,000, preferably from 1,200 to 1,800, % by weight, based on anthranilic acid. The presence of, for example, up to 5%, or somewhat more, of water, depending on the solubility, is not disadvantageous.

If the alkali metal salt of anthranilic acid is not used at the outset, an alkali metal hydroxide solution has to be added; this can be done together with the benzoyl halide or beforehand.

Suitable alkali metal hydroxide solutions are not less than 25% strength aqueous solutions of sodium hydroxide or potassium hydroxide, these being used in a roughly stoichiometric amount, for example in a ratio of from 0.9 to 1.1, in particular from 1 to 1.05, moles per mole of starting material II. Although it is also possible to carry out the procedure in a virtually anhydrous system, greater purity is achieved if an aqueous alkali solution is used.

Suitable acid halides for the cyclization reaction are thionyl chloride, phosgene, phosphorus trichloride, phosphorus pentachloride and phosphoryl chloride. The amount of the acid chloride is advantageously from 0.9 to 1.3, preferably from 0.95 to 1.15, moles per mole of starting material II where thionyl chloride or phosgene is used, and from 0.6 to 1 mole where phosphorus trichloride, phosphoryl chloride or phosphorus pentachloride is employed.

Suitable phase-transfer catalysts are quaternary ammonium salts, e.g. benzyltrimethylammonium chloride, benzyltriethylammonium chloride, benzyltri-n-butylammonium chloride, benzyltrimethylammonium hydroxide, tetraethylammonium chloride, tetraethylammonium bromide, tetrabutylammonium iodide, cetyltrimethylammonium bromide, methyltributylammonium iodide, myristyltrimethylammonium bromide, phenyltrimethylammonium iodide or tetramethylammonium tetrafluoborate, and quaternary phosphonium salts, e.g. benzyltriphenylphosphonium chloride, hexadecyltributylphosphonium bromide, methyltriphenylphosphonium bromide, methyltrioctylphosphonium chloride, dodecyltriphenylphosphonium bromide or n-propyltriphenylphosphonium bromide.

The catalyst is used in a catalytically effective amount, for example from 0.1 to 5, advantageously from 1 to 2, % by weight, based on the raw material II (aminobenzoic acid).

Advantageously, the process is carried out as follows: the benzoyl halide and an equivalent amount of aqueous alkali solution are run, via two feed lines, in the course of from 10 to 80 minutes, and at from 10° to 50° C., preferably 20° to 45° C., into the anthranilic acid, which is partly dissolved but predominantly in suspension in the suspending agent. The addition of the alkali solution may be carried out so that it is ahead of the addition of the other component, or the alkali solution may be added entirely at the outset.

The water is then removed from the reaction mixture in a conventional manner; where the suspending agent permits azeotropic distillation to be carried out, the water is removed azeotropically from the reaction mixture. In the case of fairly high-boiling suspending agents, this may also be effected under reduced pressure.

The second reaction step, cyclization with elimination of water, is then carried out, the water-binding agent used advantageously being an economical acid halide. In this case, the temperature initially required is from 20° to 80° C., after which stirring is continued at up to 140° C., preferably from 50° to 110° C. for from 1 to 3 hours until the evolution of gas has ceased. If a gaseous acid halide, e.g. phosgene, has been chosen, the procedure may be carried out directly at from 50° to 110° C. When phosgene is used as the catalyst, it is advantageous to add an amide of the N,N-dimethylformamide type in an amount of from 0.2 to 3, advantageously from 0.5 to 1, % by weight, based on anthranilic acid. In this method of water elimination, the amide character of the intermediate is lost and dissolution occurs when a suitable suspending agent is used.

To obtain the end product, the neutral salt (generally sodium chloride) precipitated in the reaction mixture, and any insoluble impurities, are filtered off under suction, and the filtrate is evaporated down. The end product obtained in this manner is sufficiently pure to be used as, for example, a herbicide or for subsequent reactions. It can of course be further purified if required, for example by distillation. In another procedure, the mixture is cooled to about 30°-50° C., excess acid chloride is decomposed by adding water, and extraction is then carried out with water or dilute aqueous alkali. The solvent-containing filtrate is again evaporated down.

The end products are useful selective herbicides (cf. German Laid-Open Application DOS No. 2,914,915) or may be used for the preparation of herbicides which are the result of further development.

EXAMPLE 1

70.3 g of benzoyl chloride and 40 g of 50% strength aqueous sodium hydroxide solution are added simultaneously via 2 feed apparatuses in the course of 40 minutes at from 23° to 42° C. to a stirred mixture of 85.8 g of finely divided 6-chloroanthranilic acid, 0.9 g of trimethylbenzylammonium chloride and 1,250 g of 1,2-dichloroethane. Stirring is continued for 90 minutes at 28° C., the mixture is refluxed for 1 hour with separation of water, and 63.1 parts of thionyl chloride are added in the course of 45 minutes at 70° C., while stirring. Stirring is continued for 90 minutes at 82° C., after which the mixture is cooled to 40° C., extracted 3 times with water and evaporated down under reduced pressure, in the final stage at 140° C. under 20 mbar, to give 126.2 g (98%) of 5-chloro-2-phenyl-4H-3,1-benzoxazin-4-one of melting point 151°-153° C. Comparison with a purified standard using HPLC shows that the purity is 96%.

EXAMPLE 2

70.3 g of benzoyl chloride and 40 g of 50% strength aqueous sodium hydroxide solution are added simultaneously via 2 feed apparatuses in the course of 40 minutes at from 20° to 35° C. to a stirred mixture of 85.8 g of 6-chloroanthranilic acid, 1.3 g of tetrabutylammonium iodide, 0.5 g of dimethylformamide and 1,300 g of 1,2-dichlorobenzene. Stirring is continued for 90 minutes at 30° C., the water is separated off at from 75° to 90° C. and under from 20 to 50 mbar and 64 g of phosgene are added via a gas inlet tube in the course of 1 hour at from 100° to 105° C., while stirring. The mixture is cooled to room temperature while nitrogen is passed through, after which insoluble substances are filtered off and the filtrate is evaporated down, in the final stage at 140° C. and under 20 mbar. Distillation at 221°-230° C. and under 4-5 mbar gives 121 g (94%) of 5-chloro-2-phenyl-4H-3,1-benzoxazin-4-one of melting point 155°-157° C. The product is 99.5% pure according to HPLC.

COMPARATIVE EXPERIMENT

The process described in J. Org. Chem. 9 (1944), 396 is used, and 28.1 g of benzoyl chloride and 100 ml of 0.2 N sodium hydroxide solution are run into a thoroughly stirred solution of 34.3 g of 6-chloroanthranilic acid in 1 l of 0.2 N sodium hydroxide solution in the course of 60 minutes at 1° C. The precipitate which separates out does not dissolve even after the temperature has increased to 25°C.; after stirring has been continued for a further 60 minutes, this precipitate is filtered off under suction and dried, 8.3 g of residue being obtained. 5 N hydrochloric acid is added dropwise to the filtrate in a 2 l beaker until crystallization begins. The mixture is then heated to 70° C., and a total of 40 ml of 5 N hydrochloric acid are added while stirring thoroughly. Thereafter, the mixture is cooled in an ice bath, 10 ml of 5 N hydrochloric acid are added and the mixture is filtered under suction. The crystals are washed with a total of 1 l of ice cold water added in portions, and are filtered off under suction and dried overnight. 32.7 g of N-benzoyl-6-chloroanthranilic acid of melting point 208°-210° C. are obtained. The major part of the residue obtained from the reaction can be dissolved in 200 ml of stirred water only after the addition of 1.4 g of sodium hydroxide. After 0.5 g of further insoluble impurities of melting point 120°-300° C. has been separated off, the filtrate obtained is acidified with 5 N hydrochloric acid in the manner described above, first at 70° C. and then at 4° C., and is washed and dried, a further 6.5 g of N-benzoylchloroanthranilic acid of melting point 208°-210° C. being obtained. The total yield is 39.2 g, or 71.5% of theory.

EXAMPLE 3

48 g of 3-trifluoromethylbenzoyl fluoride and 20 g of 50% strength aqueous sodium hydroxide solution are added simultaneously via 2 feed apparatuses in the course of 25 minutes at from 25° to 36° C. to a stirred mixture of 42.9 g of 6-chloroanthranilic acid and 0.45 g of triethylbenzylammonium chloride and 700 g of toluene. Stirring is continued for 90 minutes at 27° C., after which the water is separated off at from 87° to 104° C. After the addition of 32.7 g of thionyl chloride in the course of 15 minutes at 70° C., stirring is continued for 90 minutes at 82° C. The mixture is extracted once with water and once with 0.4 N sodium hydroxide solution, and is evaporated down to give 75 g (92%) of 5-chloro-2-(m-trifluoromethylphenyl)-4H-3,1-benzoxazin-4-one of melting point 116°-120° C.

EXAMPLE 4

When 42.9 g of 6-chloroanthranilic acid, 39.6 g of 3-fluorobenzoyl chloride, 20 g of 50% strength sodium hydroxide solution, 0.45 g of benzyltriphenylphosphonium chloride, 620 g of 1,2-dichloroethane and 32.7 g of thionyl chloride are used as starting materials and the procedure described in Example 1 is employed, 68.8 g of 5-chloro-2-(m-fluorophenyl)-4H-3,1-benzoxazin-4-one of melting point 120°–123° C. are obtained. The yield is virtually quantitative and the purity is 98% according to HPLC.

EXAMPLE 5

When 42.9 g of 6-chloroanthranilic acid, 58.4 g of 3-chlorodifluoromethoxybenzoyl fluoride, 20.8 g of 50% strength sodium hydroxide solution, 0.45 g of benzyltrimethylammonium chloride, 700 g of 1,2-dichloroethane and 32.7 g of thionyl chloride are used as starting materials and the procedure described in Example 1 is employed, 88.6 g (99%) of 5-chloro-2-(m-chlorodifluoromethoxyphenyl)-4H-3,1-benzoxazin-4-one of melting point 112°–114° C. are obtained.

EXAMPLE 6

When 38.8 g of 6-fluoroanthranilic acid, 39 g of 4-fluorobenzoyl chloride, 20 g of 50% strength sodium hydroxide solution, 0.45 g of benzyltrimethylammonium chloride, 700 g of 1,2-dichloroethane and 32.7 g of thionyl chloride are used as starting materials, and the procedure described in Example 1 is employed, 62 g (96%) of 5-fluoro-2-(p-fluorophenyl)-4H-3,1-benzoxazin-4-one of melting point 189°–193° C. are obtained.

EXAMPLE 7

33.6 g of 4-trifluoromethylmercaptobenzoyl fluoride and 12 g of 50% strength sodium hydroxide solution are added simultaneously via 2 feed apparatuses in the course of 30 minutes at from 20° to 39° C. to a stirred mixture of 25.7 g of 6-chloroanthranilic acid, 0.27 g of benzyltrimethylammonium chloride and 450 g of 1,2-dichloroethane. Stirring is continued for 90 minutes at 27° C., after which the water is separated off and 21.5 g of phosphoryl chloride are added at 70° C. Stirring is continued for 3 hours at 82° C., after which the mixture is cooled to 30° C. and extracted 3 times with water. Evaporating down the solution, in the final stage at 140° C. and under 2 mbar, gives 48.8 g (91%) of 5-chloro-2-(p-trifluoromethylmercaptophenyl)-4H-3,1-benzoxazin-4-one of melting point 135°–140° C.

EXAMPLE 8

92.3 g of benzoyl chloride and 52.6 g of 50% strength aqueous sodium hydroxide solution are introduced simultaneously via 2 feed apparatuses in the course of 40 minutes at from 22° to 38° C. to a stirred suspension of 128.6 g of 6-chloroanthranilic acid and 1.35 g of trimethylbenzylammonium chloride in 1,870 g of 1,2-dichloroethane. Stirring is continued for 30 minutes at 32° C., after which a further 16.3 g of benzoyl chloride and 9.3 g of 50% strength sodium hydroxide solution, as described above, are added in the course of 5 minutes, and the mixture is stirred for a further 55 minutes at from 25° to 30° C. The mixture is then refluxed for 1¼ hours to separate off water, this procedure being continued until the organic phase in the water separator no longer appears cloudy. 0.2 g of dimethylformamide are added, after which 96 g of gaseous phosgene are passed into the stirred refluxed mixture in the course of 1¾ hours, and excess phosgene is then expelled in the course of 5 minutes by blowing in nitrogen. After cooling to 40° C., the reaction mixture is extracted 3 times with water and once with a little concentrated sodium chloride solution. The organic phase is evaporated down under reduced pressure, in the final stage at 140° C. and under 20 mbar, 190.5 g (98.6%) of 5-chloro-2-phenyl-4H-3,1-benzoxazin-4-one of melting point 153°–156° C. being obtained. The purity according to HPLC is 97.4%.

COMPARATIVE EXPERIMENT TO EXAMPLE 8

40 g of 50% strength aqueous sodium hydroxide solution are added to a stirred suspension of 85.8 g of 6-chloroanthranilic acid in 1,250 g of 1,2-dichloroethane in the course of 10 minutes at from 20° to 30° C. The salt suspension is freed from water by refluxing it for 1 hour in a water separator. Thereafter, 56.2 g of benzoyl chloride are added in the course of 40 minutes at from 25° to 35° C., and stirring is continued for a further 30 minutes. Under the same conditions, a further 14.1 g of benzoyl chloride are added in the course of 5 minutes, and stirring is continued for 55 minutes at 25° C. 0.2 g of dimethylformamide are added, after which 64 g of gaseous phosgene are passed into the stirred, refluxed mixture in the course of 1½ hours, and excess phosgene is then expelled by blowing in nitrogen. The reaction mixture is cooled to 40° C., and extracted three times with water and once with a little concentrated sodium chloride solution. Evaporating down the organic phase, in the final stage at 140° C. and under 20 mbar, gives 115 g (89%) of 5-chloro-2-phenyl-4H-3,1-benzoxazin-4-one of melting point 148°–152° C. According to HPLC and comparison with an analytical standard, the purity is 86%.

COMPARATIVE EXPERIMENT TO EXAMPLE 8

Under reaction conditions identical to those in the above comparative experiment, but with the addition of 0.9 g of trimethylbenzylammonium chloride to the suspension of 85.8 g of 6-chloroanthranilic acid in 1,250 g of 1,2-dichloroethane, 120.9 g (93.9%) of 5-chloro-2-phenyl-4H-3,1-benzoxazin-4-one of meltlng point 152°–153° C. are obtained after the mixture has been worked up. The purity according to HPLC is 87.5%.

EXAMPLE 9

Under the reaction conditions described in Example 1, 14.4 g of m-trifluoromethylbenzoyl fluoride, 6 g of 50% strength aqueous sodium hydroxide solution, 11.6 g of 5-fluoroanthranilic acid and 0.15 g of trimethylbenzylammonium chloride in 185 g of 1,2-dichloroethane are reacted with one another, and the product is then subjected to a cyclization reaction with 11 parts of thionyl chloride. Working up the mixture gives 20.8 g (90%) of 6-fluoro-2-(m-trifluoromethylphenyl)-4H-3,1-benzoxazin-4one of melting point 118°–119° C.

EXAMPLE 10

When the reaction conditions of Example 1 are employed but 11.6 g of 4-fluoroanthranilic acid and 14.4 g of p-trifluoromethylbenzoyl fluoride are used, 21.1 g (91%) of 7-fluoro-2-(p-trifluoromethylphenyl)-4H-3,1-benzoxazin-4-one of melting point 137°–139° C. are obtained.

EXAMPLE 11

When the reaction conditions of Example 1 are employed but 11.3 g of 5-methylanthranilic acid and 13.1 g of 3-chlorobenzoyl chloride are used, 18.5 g (91%) of 6-methyl-2-(m-chlorophenyl)-4H-3,1-benzoxazin-4-one of melting point 160°–162° C. are obtained.

We claim:

1. In a process for the preparation of a 2-phenyl-4-H-3,1-benzozazin-4-one of the formula I

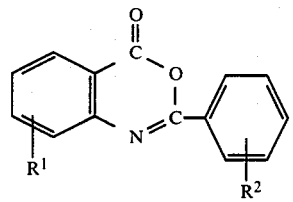 (I)

where $R^1$ is hydrogen, halogen, methyl or methoxy and $R^2$ is hydrogen, halogen or haloalkyl, haloalkoxy, haloalkylmercapto or haloalkylsulfonyl, each of 1 to 3 carbon atoms, by acylation of an antranilic acid II

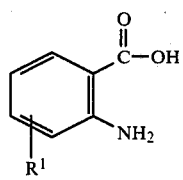 (II)

with a benzoyl halide III

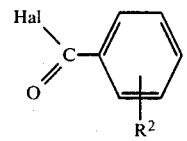 (III)

where Hal is halogen, in the presence of a base and effecting ring closure of the benzoyl anthranilate thus obtained by elimination of water, the improvement in the acylation step which comprises reacting the benzoyl halide III with (a) a mixture of a stoichiometric amount of an at least 25% strength aqueous alkali metal hydroxide solution and a suspension of the anthranilic acid II in a suspending agent which is immiscible with the aqueous alkali metal hydroxide solution or (b) a suspension of an alkali metal salt of anthranilic acid II in a suspending agent as defined under (a) in the presence of a catlytically effective amount of a phase-transfer catalyst.

2. The process as of claim 1, wherein the acylation is carried out at from 10° to 50° C.

3. The process of claim 1, wherein the anthranilic acid II is selected from the group consisting of 6-chloro-, 6-fluoro- and 6-bromo anthranilic acid, 6-methyl- and 6-methoxyanthranilic acid. 5-fluoro-, 5-bromo, 5-methyl and 5-methoxyanthranilic acid, 4-fluoro-,4-chloro-, 4-bromo-4-methyl- and 4-methoxyanthranilic acid and 3-fluoro-, 3-chloro-, 3-bromo-3-methyl- and 3-methoxyanthranilic acid.

4. The process of claim 3, wherein the benzoyl halide is benzoyl chloride of benzoyl bromide.

* * * * *